(12) United States Patent
Bartsch et al.

(10) Patent No.: US 7,737,310 B2
(45) Date of Patent: Jun. 15, 2010

(54) METHOD FOR PRODUCING BIPHENOLS FROM MONOPHENOLS

(75) Inventors: Michael Bartsch, Neustadt (DE); Gerd Haderlein, Grünstadt (DE); Tobias Aechtner, Mannheim (DE); Jens Scheidel, Hirschberg (DE); Christian Dienes, Landau (DE); Alexander Tempel, Worms (DE); Thorsten Hofrichter, Frankenthal (DE); Werner Weinle, Bad Friedrichshall (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/910,665

(22) PCT Filed: Apr. 5, 2006

(86) PCT No.: PCT/EP2006/061352

§ 371 (c)(1),
(2), (4) Date: Oct. 4, 2007

(87) PCT Pub. No.: WO2006/106123

PCT Pub. Date: Oct. 12, 2006

(65) Prior Publication Data

US 2008/0177113 A1 Jul. 24, 2008

(30) Foreign Application Priority Data

Apr. 6, 2005 (DE) .................. 10 2005 015 893

(51) Int. Cl.
*C07C 39/16* (2006.01)
(52) U.S. Cl. ................ 568/723; 568/730; 568/722; 568/727; 568/803
(58) Field of Classification Search ............ 568/730, 568/722, 803
See application file for complete search history.

(56) References Cited

U.S. PATENT DOCUMENTS 4,962,240 A * 10/1990 Kitamura et al. ............ 568/730
5,981,772 A    11/1999 Foo et al.
6,077,979 A *  6/2000 Qiu .......................... 568/730

FOREIGN PATENT DOCUMENTS

WO        03/045883  A1    6/2003
WO    WO 03/045883  A1  * 6/2003
WO       2004069779  A1    8/2004
WO       2004076464  A2    9/2004

* cited by examiner

*Primary Examiner*—Porfirio Nazario-Gonzalez
*Assistant Examiner*—Yate' K Cutliff
(74) *Attorney, Agent, or Firm*—Connolly Bove Lodge & Hutz LLP

(57) ABSTRACT

A process for preparing biphenols of the general formula I

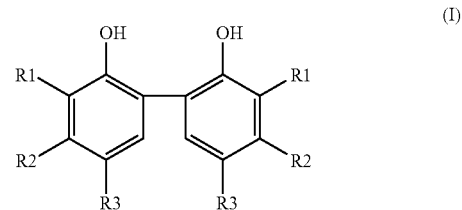

by reaction of monophenols of the general formula II

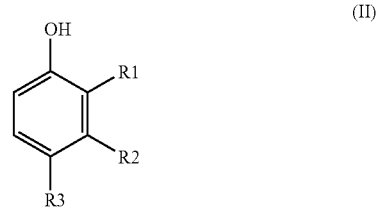

where the radicals R1, R2 and R3 are each, independently of one another, hydrogen, alkyl, aryl or arylalkyl having from 1 to 10 carbon atoms, in the presence of an oxidant in a reactor, wherein
a) the reactor comprises no stationary internals which act as baffles,
b) a total of not more than 0.6 mol of oxidant is used per one mol of monophenol, and
c) the oxidant is introduced either continuously or discontinuously in a plurality of portions over a period of from 10 minutes to 24 hours, with the amount of oxidant introduced per unit time not being constant over the total period of time but instead being varied.

20 Claims, No Drawings

METHOD FOR PRODUCING BIPHENOLS FROM MONOPHENOLS

CROSS REFERENCE TO RELATED APPLICATIONS

This application is a National Phase of International Application No. PCT/EP2006/061352 filed on Apr. 5, 2006, which claims priority to Application No. 102005015893.5 filed in Germany on Apr. 6, 2005 under 35 U.S.C. §119; the entire contents of all are hereby incorporated by reference.

DESCRIPTION

The invention relates to a process for preparing biphenols of the general formula I

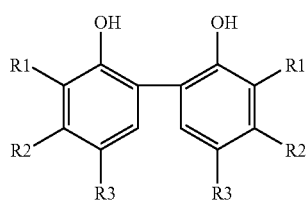

by reaction of monophenols of the general formula II

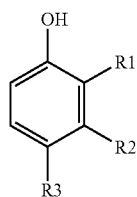

where the radicals R1, R2 and R3 are each, independently of one another, hydrogen, alkyl, aryl or arylalkyl having from 1 to 10 carbon atoms, in the presence of an oxidant in a reactor, wherein a) the reactor comprises no stationary internals which act as baffles, b) a total of not more than 0.6 mol of oxidant is used per one mol of monophenol, and c) the oxidant is introduced either continuously or discontinuously in a plurality of portions over a period of from 10 minutes to 24 hours, with the amount of oxidant introduced per unit time not being constant over the total period of time but instead being varied.

In addition, the invention relates to the biphenols which are obtainable by the process, and also their use for preparing phosphorus-comprising chelating ligands.

Unsubstituted and substituted biphenols have a variety of uses, for example as intermediates in chemical syntheses or as monomers for the preparation of polymers. Biphenols are also used for preparing catalyst systems for the hydrocyanation of pentenenitriles to adiponitrile: the catalyst system usually comprises complexes of nickel(0) with phosphorus-comprising chelating ligands, and the biphenols are starting materials in the preparation of these chelating ligands, cf. U.S. Pat. No. 5,981,772. The hydrocyanation mentioned is carried out on an industrial scale and requires considerable amounts of catalyst, which is why the biphenols are also prepared by means of industrial processes.

The biphenols are usually prepared by oxidative coupling of corresponding monophenols, but the yield of these syntheses is in need of improvement. WO-A 03/045883 describes the preparation of particular substituted biphenols using a copper-comprising catalyst.

U.S. Pat. No. 6,077,979 describes a process for preparing 3,3',5,5'-tetramethyl-2,2'-biphenol by reacting 2,4-dimethylphenol (DMP) with an oxidant (persulfate or hydrogen peroxide) in the presence of an iron catalyst at from 0 to 100° C. The molar ratio of DMP:oxidant is from 1.2:1 to 1:1.2, i.e. is approximately equimolar. On the evidence of the examples, the amounts of reactants and solvents used are not more than a few hundred grams and a few liters, respectively (Example 1); the largest reactor used is a stirred 5 liter flask. The oxidant is added either all at once at the beginning of the reaction or, in Example 1, uniformly over a period of 4 hours.

The applicant of the present patent application has scaled up the process of U.S. Pat. No. 6,077,979 to an industrial scale. This was carried out using a 2 m³ stirred vessel in which the generally customary baffles had been installed to achieve better mixing of the contents of the vessel. Unexpectedly, the following problems occurred:

The reaction products formed (phenols) stuck to the stirrer, resulting in imbalance. To avoid destruction of the stirrer, it had to be cleaned frequently. This interruption to production for the purpose of cleaning had a considerable adverse effect on the economics of the process.

Phenols formed deposited in the region behind the baffles. Production had to be interrupted and the vessel had to be cleaned.

Considerable amounts of undesirable by-products, in particular oligomeric phenol compounds, were formed. The purity of 95% reported in U.S. Pat. No. 6,077,979 for the 5 liter batch was only achieved after the product had been recrystallized twice and the yield was significantly lower than that indicated in the U.S. patent.

These by-products made the work-up of the reaction mixture considerably more difficult, since the desired biphenol could not be separated off by filtration or other solid/liquid separation methods. Even crystallization allowed the by-products to be separated off from the desired product biphenol only to an unsatisfactory extent. This caused a further deterioration in the economics of the process.

It was an object of the invention to remedy the disadvantages indicated. A process for preparing biphenols from monophenols which can be carried out without problems even on an industrial scale is to be provided. In particular, no deposits or sticky adhering material should be formed on the reactor or its agitators. The reactor should have to be switched off for the purpose of cleaning only rarely.

Furthermore, the desired biphenol should be obtained in a high purity and should be able to be separated off from the reaction mixture in a simple manner, e.g. by filtration. Finally, a smaller amount of undesired oligomeric phenols or other by-products should be formed.

We have accordingly found the process defined at the outset. In addition, the biphenols obtainable therewith and their abovementioned use have been found. Preferred embodiments of the invention are defined in the subordinate claims.

Suitable monophenols are compounds of the general formula II

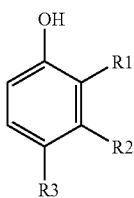

(II)

where the radicals R1, R2 and R3, hereinafter referred to collectively as R, are each, independently of one another, hydrogen, alkyl, aryl or arylalkyl having from 1 to 10 carbon atoms. Alkyl includes cycloalkyl. In addition, the radicals R can also comprise heteroatoms such as halogen, O, N, P, S or Si.

The radicals R preferably comprise from 1 to 8, in particular from 1 to 6, carbon atoms. R is particularly preferably alkyl, more preferably $C_{1-4}$-alkyl, in particular n-propyl, isopropyl, ethyl or methyl. Methyl is very particularly preferred.

Preference is given to one of the three radicals R1, R2 and R3 being hydrogen, i.e. the monophenols are preferably disubstituted by radicals R. Of the three substitution patterns 3,4 (i.e. R1=H), 2,4 (R2=H) and 2,3 (R3=H), preference is given to the 2,4-substituted monophenols (R2=H).

In a preferred embodiment, two of the radicals R1, R2 and R3 are methyl and one radical is hydrogen. In particular, R1 and R3 are methyl and R2 is hydrogen, i.e. the monophenol is preferably 2,4-dimethylphenol and the biphenol obtained therefrom is preferably 3,3',5,5'-tetramethyl-2,2'-biphenol.

The monophenols mentioned can be obtained in a manner known per se by alkylation or arylation of phenol with alkenes, alcohols or alkyl halides or aryl halides, or can be procured as commercial products.

Suitable oxidants are all compounds comprising a peroxy group —O—O—.

Preference is given to peroxodisulfates (also referred to as persulfates) of the general formula $M_2S_2O_8$, where M is ammonium or an alkali metal. M is preferably ammonium, sodium or potassium.

Further suitable oxidants are peroxides, for example inorganic peroxides such as hydrogen peroxide or metal peroxides $M^I_2O_2$ ($M^I$ is a monovalent metal), e.g. $Na_2O_2$, or $M^{II}O_2$ ($M^{II}$ is a divalent metal), e.g. $BaO_2$.

Organic peroxides, for example hydroperoxides R—O—OH, "genuine" peroxides R—O—O—R such as di-tert-butyl peroxide or dicumyl peroxide, diacyl peroxides R—C(O)—O—O—C(O)—R such as dibenzoyl peroxide or diacetyl peroxide, peracids R—C(O)—O—OH such as m-chloroperbenzoic acid, esters of peracids R—C(O)—O—O—R*, ketone peroxides such as acetone peroxide and epidioxides (endoperoxides) such as 3,3,4,4-tetramethyl-1,2-dioxethane, where R or R* is alkyl, aryl or arylalkyl having from 1 to 30 carbon atoms, are also suitable.

Particular preference is given to using a peroxodisulfate or a peroxide as oxidant. Sodium peroxodisulfate $Na_2S_2O_8$ is particularly useful.

It goes without saying that mixtures of various oxidants can also be employed.

According to the invention, a total of not more than 0.6 mol of oxidant is used per one mol of monophenol (of the general formula II above). The lower limit to the amount of oxidant depends on the desired conversion. Preference is given to using a total of from 0.45 to 0.6 mol, in particular from 0.49 to 0.55 mol, of oxidant per one mol of monophenol. If mixtures of a plurality of oxidants are used, the amounts specified are based on the sum of all oxidants.

In the abovementioned prior art U.S. Pat. No. 6,077,979, about 1 mol of persulfate or peroxide were used per 1 mol of 2,4-dimethylphenol, i.e. an amount of oxidant far above the stoichiometric amount. In contrast, it can be seen from the amounts indicated according to the invention that a considerably lower, preferably approximately stoichiometric, amount of oxidant is used in the present invention, which gives significantly better results.

Further details regarding the addition of the oxidant are given below.

A metal or a metal compound in a catalytically effective amount is usually used in addition to the oxidant. However, the metal or the metal compound is not absolutely necessary. Suitable metals/metal compounds are, in particular, iron, copper and their compounds. The metal can be used as such or as an alloy. Suitable metal compounds are, for example, the halides, sulfates, nitrates, phosphates or cyanides, e.g. as such or in the form of their hydrates.

Particular preference is given to using iron or iron compounds, in particular iron(II) compounds such as iron(II) sulfate.

If a metal or a metal compound is used, the amount is usually not critical and is usually such that the metal or the metal compound can act as catalyst. In general, this amount is from 1 to 20 mol %, based on the monophenol used.

The oxidants and the metal or the metal compound can be prepared in a manner known per se or are commercially available, and can be used as such, for example as a solid, or as a solution or suspension. Well-suited solvents for the oxidant and, if appropriate, the metal (compound) are, for example, water or water-miscible compounds, for instance for peroxodisulfates as oxidants.

The reaction of the monophenol to form the biphenol is preferably carried out in solution or suspension. Preferred solvents or suspension media are polar liquids, for example water, isopropanol, methyl tert-butyl ether (MTBE) or acetonitrile. Water is preferred and is used, for example, as deionized water.

It has been found that particularly good results are achieved when the amount of monophenol used is from 5 to 20% by weight, based on the sum of all starting materials. The starting materials include, for example, the monophenol and the oxidant and auxiliaries such as the catalytically active metal or the metal compound and also the solvent or suspension medium.

The reaction temperature is usually from 0 to 95° C., preferably from 20 to 70° C., in particular from 40 to 60° C. The pressure is usually not critical and is from 1 mbar to 100 bar, preferably from 0.1 to 10 bar.

The process of the invention can be carried out continuously or preferably discontinuously in any customary reactor, and it is in principle possible to use backmixing or nonbackmixing reactors (i.e. reactors having stirred tank characteristics or tube reactor characteristics). Examples of suitable reactors are stirred vessels, tower reactors, loop reactors and also tube reactors or shell-and-tube reactors, which can be operated individually or as a cascade. The reactor is preferably a stirred vessel.

According to the invention, the reactor comprises no internals which act as baffles, in particular no stationary or movable baffles, no heat exchangers which dip into the reaction mixture and act as baffles nor any similar components. For the purposes of the invention, a stirrer which may be used for achieving better mixing of the contents of the reactor does not count among "internals which act as baffles" i.e. according to the invention, it is quite possible to use a stirrer, as is the case for a stirred tank reactor.

Suitable stirrers for the stirred tank reactor are, for example, disk, impeller, crossed beam, mesh, blade, inclined blade, anchor, paddle, propeller, MIG, inter-MIG or helical stirrers or other customary types. The conditions, in particular the type, size and shape of the stirred vessel and of the stirrer and also the stirrer speed are preferably selected so that an air bubble is formed in the reaction mixture in the region of the stirrer when the stirrer is switched on.

According to the invention, the oxidant, i.e. the total amount of the oxidant, is introduced either continuously or discontinuously in a plurality of portions over a period of from 10 minutes to 24 hours. This period is preferably from 30 minutes to 12 hours, in particular from 2 to 10 hours. The period depends, inter alia, on the amounts of starting material used, the type and amount of solvents or suspension media used, the reaction temperature and pressure and the desired reaction time.

Likewise according to the invention, the amount of oxidant introduced per unit time (e.g. per minute or per hour) is not constant over the entire period of time but is instead varied. The following specific numerical data (hours, kilograms, etc.) are only for the purposes of illustration and do not restrict the scope of the invention:

In the case of discontinuous addition and a total time of addition of, for example, 8 hours, it is possible, for example, to add a first portion of 30 kg of oxidant at the beginning (t=0), a second portion of 20 kg after two hours (t=2 h), a third portion of 5 kg after a further three hours (t=5 h) and a fourth and final portion of 25 kg after a further three hours (t=8 h), i.e. the individual portions and/or the time intervals between them are not all equal in the case of discontinuous addition.

In the case of continuous addition, which is preferred, the amount of oxidant added, when plotted, for example, as oxidant stream in [kg/min] or [mol/min] versus time in [h], can be according to, for example, an ascending or descending function, a step function, an exponential function, a function having one or more minima or maxima or a function obeying another mathematical relationship, as long as the oxidant stream is different at at least two points in time. If the addition is, for example, according to a step function and an addition time of a total of 8 hours, the oxidant can, for example, be added at 2 kg/h for the first 2 hours, then at 0.5 kg/h for 4 hours and finally at 1.5 kg/h for the last 2 hours.

Mixed forms of continuous and discontinuous addition are also possible. For example, it is possible to add the oxidant continuously during the first 3 hours of a total addition time of 8 hours, then add no oxidant for 2 hours and add oxidant continuously again for the last 3 hours, or else add oxidant discontinuously in two portions during the last 3 hours.

In a preferred embodiment of the process, the amount of oxidant introduced per unit time is x at the beginning of the reaction until a conversion of 20% has been reached, then is y until a conversion of 40% has been reached and finally is z at a conversion of above 40%, where: x>y and z>y.

In other words, the amount introduced up to a conversion of 20% and that introduced at a conversion of above 40% is preferably in each case higher than at a point in time in between. x and z can be identical or different and the amount of oxidant x, y and z can, for example, be expressed as a molar amount, mass, volume, molar flow, mass flow or volume flow.

Preference is likewise given to the relationship y≦0.5 x and y≦0.5 z being satisfied, i.e. the amount of oxidant introduced per unit time at a point in time in the range from >20 to 40% conversion is preferably not more than half the amount x introduced up to a conversion of 20% and not more than half the amount z introduced at a conversion of above 40%.

The reaction is preferably not carried out to complete conversion but instead to a conversion of not more than 95%, particularly preferably not more than 90%, based on the monophenol used.

After the end of the addition of oxidant, i.e. after the addition time has elapsed, an after-reaction time (in the case of stirred tank reactors also referred to as further stirring) can be provided, depending on the reaction temperature and amount of starting material, to allow the reaction to proceed to the desired conversion.

The reaction mixture is subsequently worked up in a conventional manner to isolate the biphenol obtained. If the reaction is, as is preferred, carried out in a polar, in particular aqueous medium, the biphenol is usually extracted from the reaction mixture by addition of an extractant. Suitable extractants are, in particular, aliphatic, araliphatic or aromatic hydrocarbons. Examples of suitable hydrocarbons are toluene, cyclohexane, methylcyclohexane and $C_{5-10}$-alkanes such as the heptanes. In this extraction, the temperature can be adapted if necessary and the reaction mixture can be extracted one or more times with identical or different extractants.

The extracted biphenol can then be separated off from the organic phase by customary separation methods. For example, the biphenol can be precipitated by cooling and separated off from the resulting suspension by filtration or other solid-liquid separation processes.

When the process of the present invention is used, a biphenol of high purity is in many cases obtained after only a single crystallization and simple filtration. Multiple crystallization to separate off by-products or complicated separation processes are not necessary.

If necessary, the biphenol which has been separated off can be washed, e.g. with the abovementioned extractants, or freed of any impurities in another way to purify it further, and finally dried.

The process of the invention avoids the abovementioned disadvantages of the prior art. The deposition of sticky reaction products on the stirrer and in the reactor is substantially reduced and the reactor has to be switched off for the purposes of cleaning only rarely. The desired product biphenol can be isolated in good purity in a technically simple manner by means of a single crystallization and filtration. The purity of the biphenol obtained is also satisfactory when the reaction is carried out on an industrial scale.

The invention likewise provides the biphenols obtainable by the process of the invention and also provides for the use of the biphenols as described at the outset for preparing phosphorus-containing chelating ligands.

EXAMPLES

Example A According to the Invention

A 2 m³ stirred enameled steel vessel which has a heatable outer wall and comprises no baffles or other internals was used. The vessel was equipped with an inclined blade stirrer which was operated at 90 revolutions per minute.

760 kg of deionized water were placed in the reaction vessel, 13.9 kg (50 mol) of iron(II) sulfate heptahydrate were added and the solution was heated to a reaction temperature of 50° C. After addition of 122 kg (1000 mol) of 2,4-dimethylphenol, a total of 619 kg of a 19% strength by weight $Na_2S_2O_8$ solution (=500 mol of $Na_2S_2O_8$) was introduced as follows:

201 kg of solution in 1 hour, corresponding to 3.35 kg of solution per minute, then 210 kg of solution in 4 hours, corresponding to 0.88 kg of solution per minute, and finally 208 kg of solution in 1 hour, corresponding to 3.47 kg of solution per minute.

After the end of the metered addition, the reaction mixture was stirred at 50° C. for another 1 hour, subsequently heated to 70° C. and 98 kg of toluene were added. 600 kg of the aqueous phase were drained from the reactor, 300 kg of n-heptane were added to the remaining toluene/aqueous phase mixture at 70° C. and the remaining aqueous phase was also drained off. The organic phase remaining in the vessel was cooled to 20° C. at a cooling rate of 10° C. per hour. This gave a suspension which was filtered through a Seitz filter. The filter cake was washed once with 60 kg of n-heptane and dried on drying trays at 50° C. in a vacuum drying oven.

The table reports the yield of 3,3'5,5'-tetramethyl-2,2'-biphenol obtained and the product purity determined by gas chromatography using an internal standard.

Comparative Example CB was carried out by a method based on Example 1 in column 2, lines 32-47, of U.S. Pat. No. 6,077,979. Example 1 was scaled up from the 5 l laboratory flask used there to the 2 m³ stirred vessel; this corresponded to a scale-up factor 1000 based on 2,4-dimethylphenol.

The procedure of the inventive Example A of the present patent application was repeated, with the following differences:
the reaction temperature was 25° C.,
672 kg of a 35% strength by weight $Na_2S_2O_8$ solution (=1000 mol of $Na_2S_2O_8$) were added,
the $Na_2S_2O_8$ solution was introduced at a constant rate of 2.8 kg per hour over a period of 4 hours,
the reaction mixture was stirred further at 25° C. for 72 hours,
the product had to be recrystallized twice.

Comparative Example CC

The procedure of Example CB was repeated, but the stirred vessel comprised built-in baffles. A sticky solid deposited on the stirrer and in the region behind the baffles and this had to be removed after emptying the vessel.

TABLE

Results (C—comparative)

| Example | Yield*[)] | Purity |
|---|---|---|
| A | 74 kg = 61% | >98% |
| CB | 55 kg = 45% | 95% |
| CC | experiment stopped | experiment stopped |

*[)]% = % of theory

The examples show that both the yield and the product purity were significantly higher in the process according to the invention (Example A) than in the case of the procedure which is not according to the invention of Examples CB (excess of oxidant and constant addition) and CC (with baffles). These advantages could be achieved at a significantly shorter reaction time: the after-reaction time in Example A was 1 hour instead of the 72 hours in Example CB.

In Comparative Example CB, the purity of 95% was achieved only after the product had been recrystallized twice, and the yield was low at 45%. In contrast, the purity in Example A according to the invention was above 98% without recrystallization at a yield of 61%.

The invention claimed is:

1. A process for preparing biphenols of the general formula I

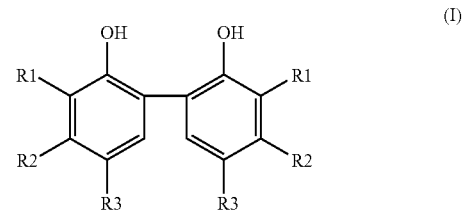

by reaction of monophenols of the general formula II

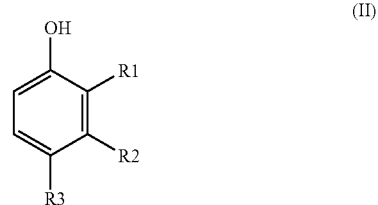

where the radicals R1, R2 and R3 are each, independently of one another, hydrogen, alkyl, aryl or arylalkyl having from 1 to 10 carbon atoms, in the presence of an oxidant in a reactor, wherein
  a) the reactor comprises no stationary internals which act as baffles,
  b) a total of not more than 0.6 mol of oxidant is used per one mol of monophenol, and
  c) the oxidant is introduced either continuously or discontinuously in a plurality of portions over a period of from 10 minutes to 24 hours, wherein the oxidant is introduced at a rate not being constant over the period but instead being varied.

2. The process according to claim 1, wherein two of the radicals R1, R2 and R3 are methyl and one radical is hydrogen.

3. The process according to claim 1, wherein the monophenol is 2,4-dimethylphenol and the biphenol is 3,3',5,5'-tetramethyl-2,2'-biphenol.

4. The process according to claim 1, wherein the oxidant is a peroxodisulfate or a peroxide.

5. The process according to claim 1, wherein the reactor is a stirred vessel.

6. The process according to claim 1, wherein the amount of monophenol used, based on the sum of all starting materials, is from 5 to 20% by weight.

7. The process according to claim 1, wherein a total of from 0.45 to 0.6 mol of oxidant is used per one mol of monophenol.

8. The process according to claim 1, wherein the amount of oxidant introduced per unit time is x at the beginning of the reaction until a conversion of 20% has been reached, then is y until a conversion of 40% has been reached and finally is z at a conversion of above 40%, where: x>y and z>y.

9. The process according to claim 8, wherein:
y≦0.5 x and y≦0.5 z.

10. The process according to claim 1, wherein the reaction is carried out to a conversion of not more than 95%.

11. The process according to claim 1, wherein the reaction is carried out at a temperature of from 40 to 60° C.

12. The process according to claim 2, wherein the monophenol is 2,4-dimethylphenol and the biphenol is 3,3',5,5'-tetramethyl-2,2'-biphenol.

13. The process according to claim 2, wherein the oxidant is a peroxodisulfate or a peroxide.

14. The process according to claim 3, wherein the oxidant is a peroxodisulfate or a peroxide.

15. The process according to claim 2, wherein the reactor is a stirred vessel.

16. The process according to claim 3, wherein the reactor is a stirred vessel.

17. The process according to claim 4, wherein the reactor is a stirred vessel.

18. The process according to claim 2, wherein the amount of monophenol used, based on the sum of all starting materials, is from 5 to 20% by weight.

19. The process according to claim 3, wherein the amount of monophenol used, based on the sum of all starting materials, is from 5 to 20% by weight.

20. The process according to claim 4, wherein the amount of monophenol used, based on the sum of all starting materials, is from 5 to 20% by weight.

* * * * *